US008192378B2

(12) United States Patent
Ootani et al.

(10) Patent No.: US 8,192,378 B2
(45) Date of Patent: Jun. 5, 2012

(54) TOE MASSAGE DEVICE

(75) Inventors: Takesaburou Ootani, Osaka (JP); Hisayuki Mori, Osaka (JP)

(73) Assignee: Eiko Enterprise Co., Ltd., Osaka (JP)

( * ) Notice: Subject to any disclaimer, the term of this patent is extended or adjusted under 35 U.S.C. 154(b) by 880 days.

(21) Appl. No.: 12/159,168

(22) PCT Filed: Dec. 28, 2005

(86) PCT No.: PCT/JP2005/024055

§ 371 (c)(1), (2), (4) Date: Jun. 25, 2008

(87) PCT Pub. No.: WO2007/077596

PCT Pub. Date: Jul. 12, 2007

(65) Prior Publication Data

US 2010/0228169 A1 Sep. 9, 2010

(51) Int. Cl.

| | |
|---|---|
| ***A61F 5/14*** | (2006.01) |
| ***A61H 1/00*** | (2006.01) |
| ***A61H 1/02*** | (2006.01) |
| ***A61H 5/00*** | (2006.01) |

(52) U.S. Cl. ................. 601/23; 601/29; 601/32; 36/141

(58) Field of Classification Search .................. 601/112, 601/118, 126, 119, 46, 116, 101–104, 122, 601/5, 27–33, 90, 93, 133, 134, 23; 36/140, 36/141, 145; 15/104.92, 161, 237; 128/845, 128/103.1, 108.1

See application file for complete search history.

(56) References Cited

U.S. PATENT DOCUMENTS

| | | | | |
|---|---|---|---|---|
| 2,397,428 | A * | 3/1946 | Moshier | 601/27 |
| 2,520,307 | A * | 8/1950 | Dorrance | 601/27 |
| 3,035,570 | A * | 5/1962 | Nelson | 601/31 |

(Continued)

FOREIGN PATENT DOCUMENTS

JP 58212442 A 12/1983

(Continued)

OTHER PUBLICATIONS

State Intellectual Property Office of People's Republic of China, Chinese Office Action (and partial English translation), mailed Mar. 11, 2010, 7 pp.

(Continued)

*Primary Examiner* — Patricia Bianco
*Assistant Examiner* — George N Phillips
(74) *Attorney, Agent, or Firm* — Eckert Seamans Cherin & Mellott, LLC; Kirk D. Houser

(57) ABSTRACT

A toe massage device is constructed from a rotating body while being supported on a base by a supporting shaft; a rotation drive device for rotating the rotating body in the normal and reverse directions; and toe fixation means provided on the rotating body and fixing toes of a subject. The toes are fixed on the rotating body by the toe fixation means and the rotating body is rotated in the normal and reverse directions. When the rotating body is rotated in the normal direction, the toes are pulled forward and downward. That is, the toes are pulled in the direction in which they are bent toward the sole. When the rotating body is rotated in the reverse direction, the toes are bent upward while being caused to move backward.

6 Claims, 8 Drawing Sheets

U.S. PATENT DOCUMENTS

| | | | | |
|---|---|---|---|---|
| 3,103,925 | A * | 9/1963 | Vogt | 601/61 |
| 6,811,539 | B1 * | 11/2004 | Nguyen | 601/31 |

FOREIGN PATENT DOCUMENTS

| | | | |
|---|---|---|---|
| JP | SHO.62-15362 | | 1/1987 |
| JP | 2-32286 | | 9/1990 |
| JP | 07-096017 | | 4/1995 |
| JP | 10-314258 | | 12/1998 |
| JP | 11-155923 | | 6/1999 |
| JP | 11-239596 | | 9/1999 |
| JP | 11-239597 | | 9/1999 |
| JP | 11239597 | A * | 9/1999 |
| JP | 2000-157596 | | 6/2000 |
| JP | 2002-119563 | | 4/2002 |
| JP | 2002-306568 | | 10/2002 |

OTHER PUBLICATIONS

Intellectual Property Office, United Kingdom Examination Report, May 17, 2010, 3 pp.

* cited by examiner

TOE MASSAGE DEVICE

FIELD OF THE INVENTION

The present invention relates to a device that applies a force bending toes to the sole side and a force bending the same back to the instep side to perform massage.

BACKGROUND ART

There have been proposed various types of toe massage devices, such as one that presses toes from above and below, or pulls the same forward to perform massage.

FIGS. 8 and 9 show one example of the toe massage devices (Patent Document 1). In this example, a pair of brackets (91) (91) is disposed on a base (9), and two roller shafts (93) (93) each having a roller (92) are disposed between both the brackets (91) (91) so as to be opposed vertically. End portions of both the roller shafts (93) (93) are biased in directions approaching each other by springs (94) (94). A guide line (95) is provided on the base (9), and a spherical body (96) is rollably provided on the guide line (95). A sole is rested on the spherical body (96) and toes are forcibly inserted between the rollers (92) (92) to be moved back and forth. The pressure from above and below by the rollers (92) (92), and the rubbing from the rollers (92) (92) by the back and forth movement of a foot are applied to the toes, thereby to perform the massage.

Patent Document 1: Japanese Patent Application Laid-Open No. 2003-119563

DISCLOSURE OF THE INVENTION

Problems to be Solved by the Invention

In the above-described toe massage device, a subject needs to move his or her foot back and forth. Accordingly, it is a bother, and hard to use in a case where the subject sits in a chair.

Moreover, the pressing the toes from above and below and the rubbing by moving the toes back and forth are a normal method in a mechanical massage, and thus, lacks novelty.

The present invention discloses a massage device capable of automatically applying a force bending toes to the sole side, and a force bending the toes back to the instep side, so that a massage effect can be obtained as if a subject were massaged by a massager.

Means for Soling the Problems

A toe massage device is made up of a rotating body (2) disposed on a base (1) rotatably in normal and reverse directions, a rotation drive device (8) that rotates the rotating body in the normal and reverse directions, and toe fixation means (7) provided on the rotating body (2) for fixing toes of a subject on the rotating body (2).

In the toe massage device, a base end of a footrest (3) for resting a foot is pivotally supported on the base (1), a free end thereof is disposed toward a rotating body (2) side on the base (1), and the footrest (3) is linked to the rotating body (2) so that the free end of the footrest (3) swings vertically in conjunction with the rotation of the rotating body (2).

The footrest (3) of the toe massage device is made up of a swinging member (4) that is linked to the rotating body (2) so that a free end thereof swings vertically, a rotating member (5) that rotates centering around a pivot (51) in a plane of the swinging member (4), and a sole rest member (6) that is disposed so as to approach, and draw apart from, the rotating body (2) on the rotating member (5) and on which a sole is rested.

In the toe massage device, the toes are fixed on the rotating body (2) by the toe fixation means (7), and the rotating body (2) is rotated alternately in the normal and reverse directions by the rotation drive device (8). In this case, when the rotating body (2) is rotated in the normal direction, the toes are pulled forward and downward. That is, the toes are pulled in a direction bending the toes to the sole side. When the rotating body (2) is rotated in the reverse direction, the toes are bent upward while being moved back.

When the rotating body (2) rotates in the normal and reverse directions, respectively, the bending to the sole side and the bending-back to the instep side of the toes are performed alternately. Additionally, these operations also involve the motions of the pull and compression of the toes, and these combined motions cannot be attained in a conventional automatic massage device, which makes the subject feel as if he or she were massaged by a massager.

Moreover, the subject only needs to fix his or her toes on the rotating body (2), and since the rotating body (2) is automatically rotated in the normal and reverse directions to perform massage by the rotation drive device (8), the subject can receive the massage in a comfortable position while sitting on a chair.

Moreover, in the toe massage device, since the free end, that is, the toe side of the footrest (3) swings in conjunction with the rotation of the rotating body (2) so as to follow the motion of the toes, large load is not applied to the toes, which can prevent the toes from being hurt.

Since in the footrest (3), the rotating member (5) can be rotated to change the orientation of the toes with respect to the toe fixation means (7) so that all the five toes are fixed on the rotating body (2) by the toe fixation means (7), the above-described massage effect can be simultaneously obtained for the five toes.

Furthermore, when the toes are pulled forward by the rotation of the rotating body (2), the sole rested on the sole rest member (6) follows the motion of the toes and goes forward to the rotating body (2) side, and additionally, the sole rest member (6) rises together with the swinging member (4), which can effectively prevent the toes from being hurt even if the toes are pulled too much.

DESCRIPTION OF REFERENCE NUMERALS

1. base

Figure 1:
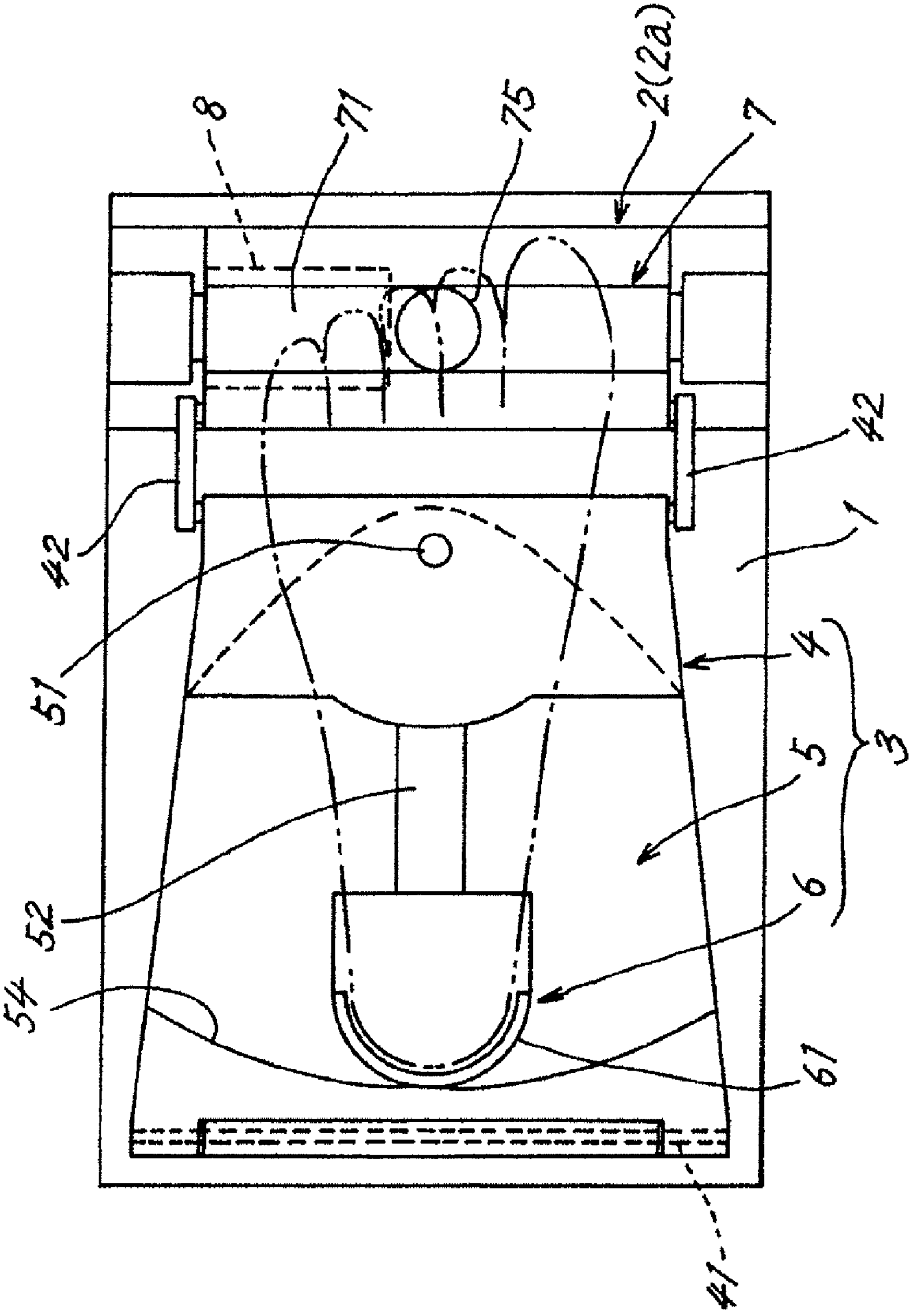
FIG. 1 is a plan view of a toe massage device.

2. rotating body 3. footrest
4. swinging member
5. rotating member
6. sole rest member
7. toe fixation means
8. rotation drive device

BEST MODE FOR CARRYING OUT THE INVENTION

A toe massage device of the present invention is shown in FIGS. 1, 2, 3, and 4. This is made up of a rotating body (2) disposed on one end side of a substantially rectangular base (1), a footrest (3) that is supported so as to vertically swing centering around a spindle (41) on the other end side on the base (1), and is linked to the rotating body (2) at a free end thereof so as to vertically swing in conjunction with the rotation of the rotating body (2), and toe fixation means (7) that is provided on the rotating body (2) for fixing the toes of a subject on the rotating body (2).

The base (1) is sized so that the entire sole of the subject can be rested thereon with an enough margin. In the base (1), brackets (11) (11) are projected on both sides of one end, and the rotating body (2) is rotatably supported by a lateral supporting shaft (21) bridging between the brackets (11) (11). The rotating body (2) of an embodiment is a roller (2*a*) having a diameter of about 6 cm and a length of about 14 cm. A rotation drive device (8) for rotating the rotating body in normal and reverse directions is linked to the roller (2*a*), and the roller (2*a*) of the embodiment is a so-called motor roller containing the rotation drive device (8).

Figure 3:
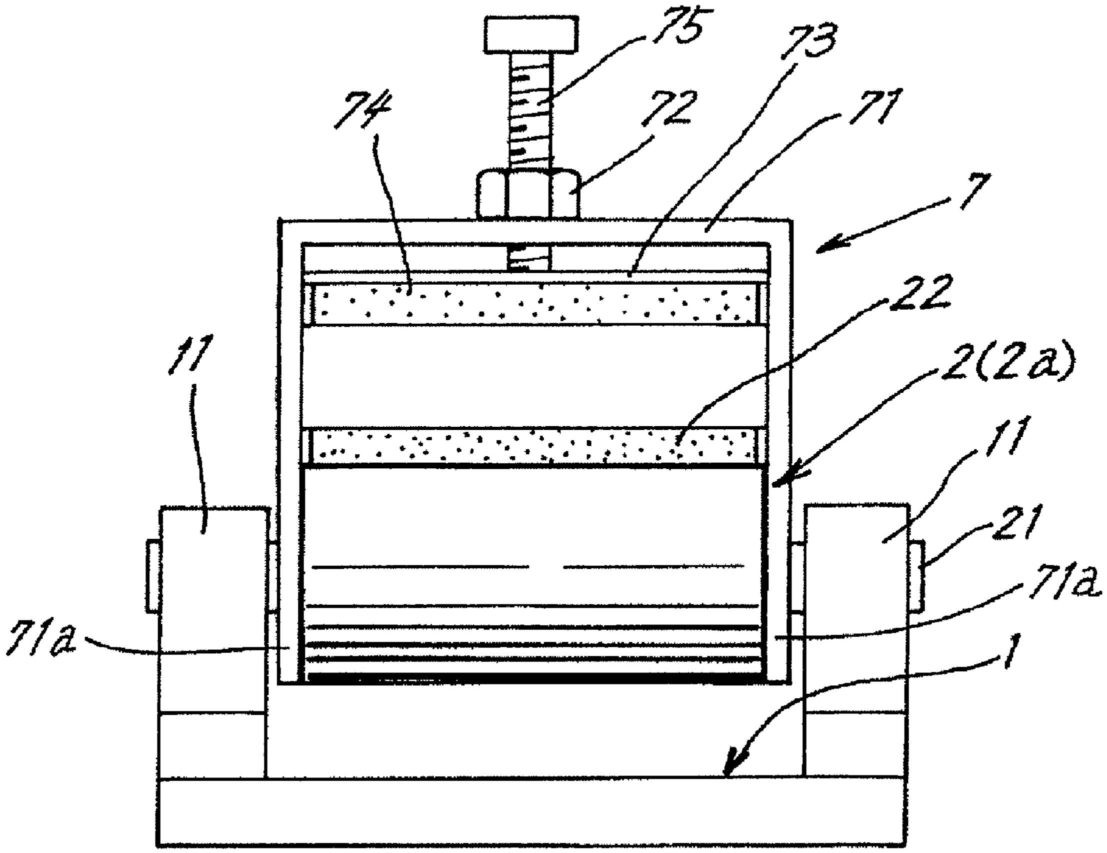
FIG. 3 is a right side view of the same.

In the toe fixation means (7) on the rotating body (2), both leg portions (71*a*) (71*a*) of a gate-shaped attachment frame (71) are fixed to both ends of the roller (2*a*), as shown in FIG. 3. A boss (72) with a screw hole is projected in a center of the attachment frame (71), and a push bolt (75) is screwed into the boss (72).

A pressing member (73) is disposed across both the leg portions (71*a*) (71*a*) in the attachment frame (71) so as to approach, and draw apart from, the rotating body (2), and a tip portion of the push bolt (75) is joined pivotably to the pressing member (73).

Elastic members (74) (22) of urethane foam resin or the like are placed in portions opposed to the pressing member (73) and the rotating body (2) surface, respectively.

As illustrated in FIG. 1, the footrest (3) is made up of a swinging member (4) that swings at a free end on the rotating body (2) side in conjunction with the rotation of the rotating body (2), a rotating member (5) disposed rotatably on the swinging member (4), and a sole rest member (6) that, on the rotating member (5), approaches, and draws apart from, the rotating body (2).

Figure 4:
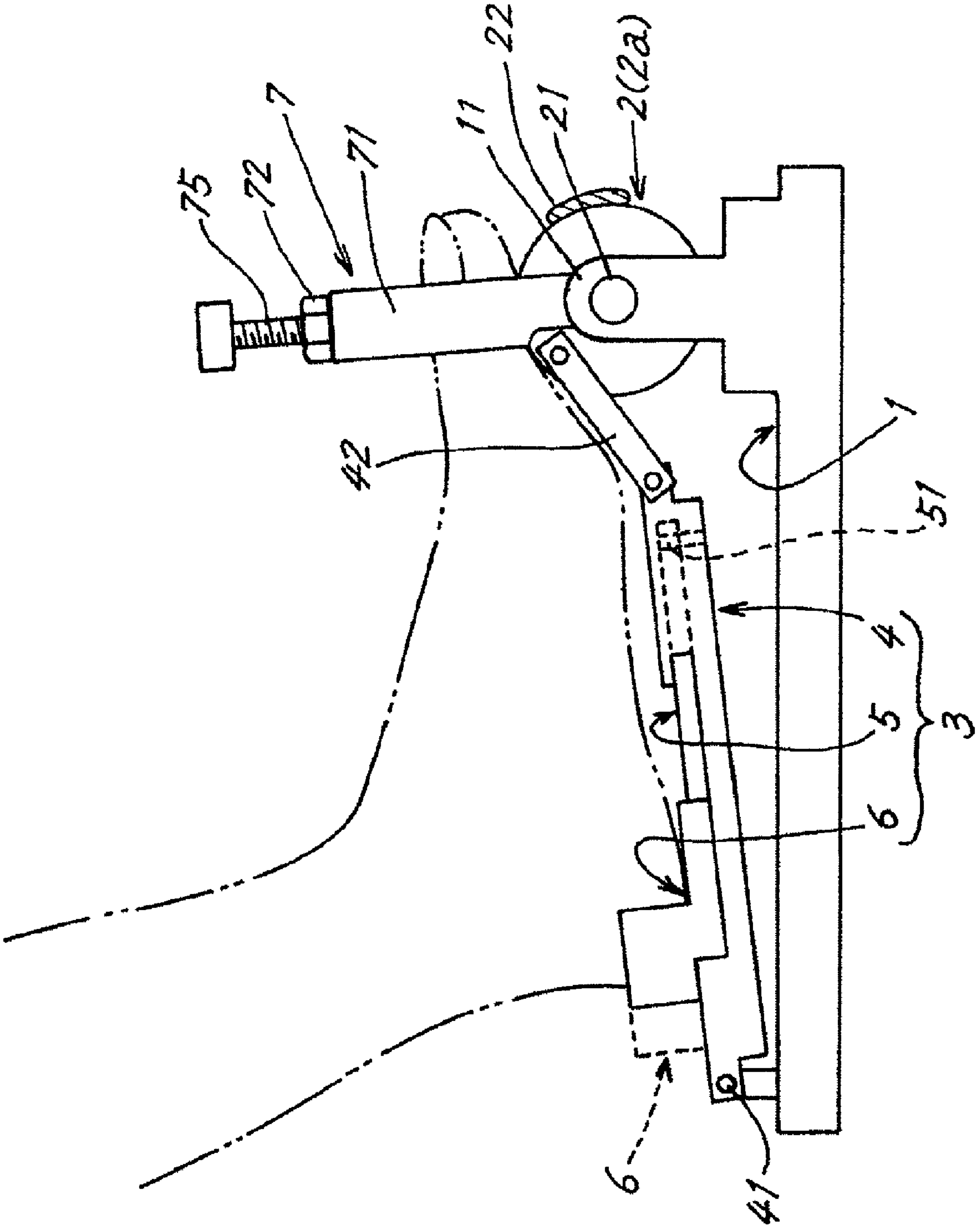
FIG. 4 is a side view of the toe massage device in which a rotating body is in a neutral position.

The swinging member (4) is a plate body, and as shown in FIG. 4, the free end thereof on the rotating body (2) side can swing vertically centering around the horizontal spindle (41) on the base (1) on the opposite side of the rotating body (2). In the swinging member (4), the free end side thereof and eccentric points of the rotating body (2) are pivotally joined through links (42).

In an upper surface of the swinging member (4), a guide depressed portion (43) (see FIG. 2) is formed, and the rotating member (5) is fitted into the guide depressed portion (43) so as to rotate centering around a pivot (51).

The above-mentioned pivot (51) is located in a center of width on the free end side of the swinging member (4) and is oriented in a direction perpendicular to the supporting shaft (21) of the rotating body (2). The rotating member (5) can rotate in a surface parallel to a plate surface of the swinging member (4). In the guide depressed portion (43) of the swinging member (4) and the rotating member (5), circular arc wall surfaces (44), (54) are formed, respectively, so that the rotating member (5) rotates with the circular arc wall surface (54) in contact with the circular arc wall surface (44).

Figure 7:
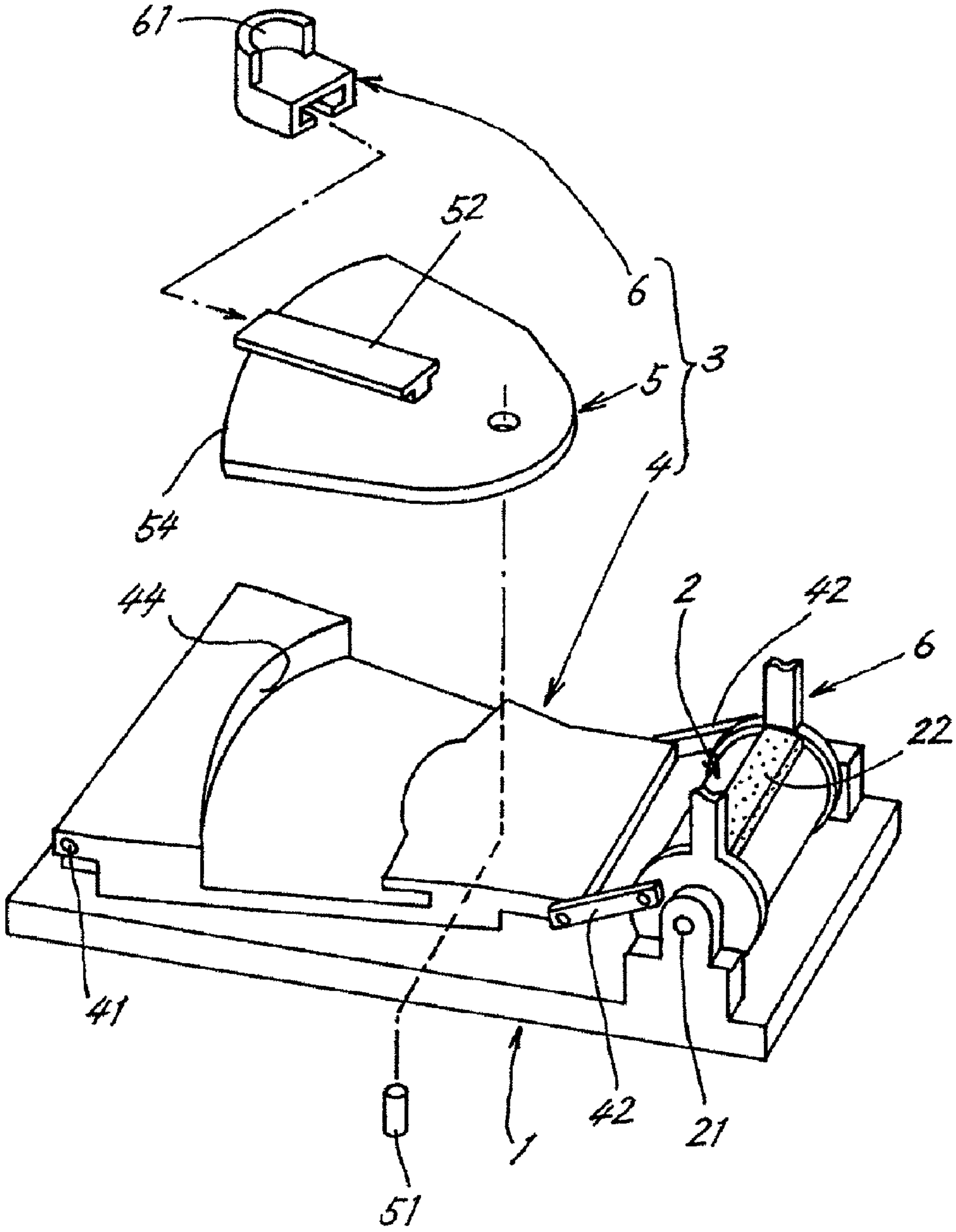
FIG. 7 is a perspective view of the toe massage device in a state where a rotating member and a sole rest member are detached.
Figure 8:
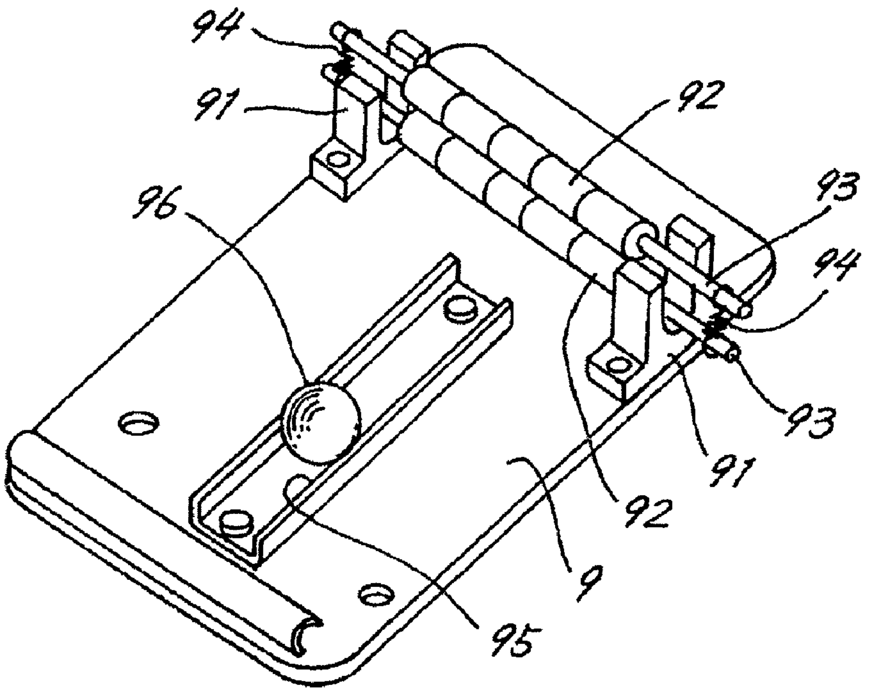
FIG. 8 is a perspective view of a conventional toe massage device.
Figure 9:
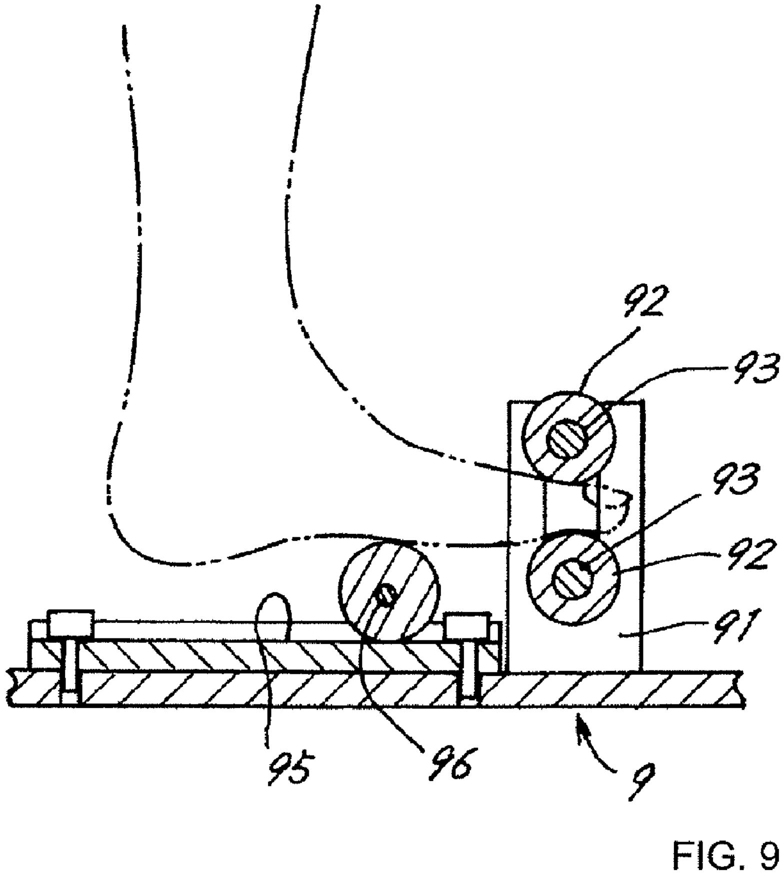
FIG. 9 is an explanatory view of a usage state of the same.

A guide line (52) is provided on the rotating member (5), and the sole rest member (6) for resting the sole is slidably provided on the guide line (52). FIG. 7 is a perspective view of the toe massage device in a state where the rotating member (5) and the sole rest member (6) are detached therefrom. The guide line (52) extends from a central portion of the circular arc wall surface (54) of the rotating member (5) to the pivot (51) side as the rotation center. The sole rest member (6) of the embodiment is formed in an enough size to rest a heel of the subject, and in the sole rest member (6), a circular arc wall (61) surrounding an outer periphery of the heel is provided vertically.

FIG. 4 shows a state where the rotating body (2) is in a neutral position. The neutral position of the rotating body (2) is a rotation stating position on the rotating body (2), in which the attachment frame (71) of the toe fixation means (7) is substantially upright. The free end of the swinging member (4) is pulled by the links (42), and as compared with a case where the free end rises most, it rises to about a half height.

The rotation drive device (8) causes the rotating body (2) to stop in the neutral position when an operation switch (not shown) is turned off.

Figure 5:
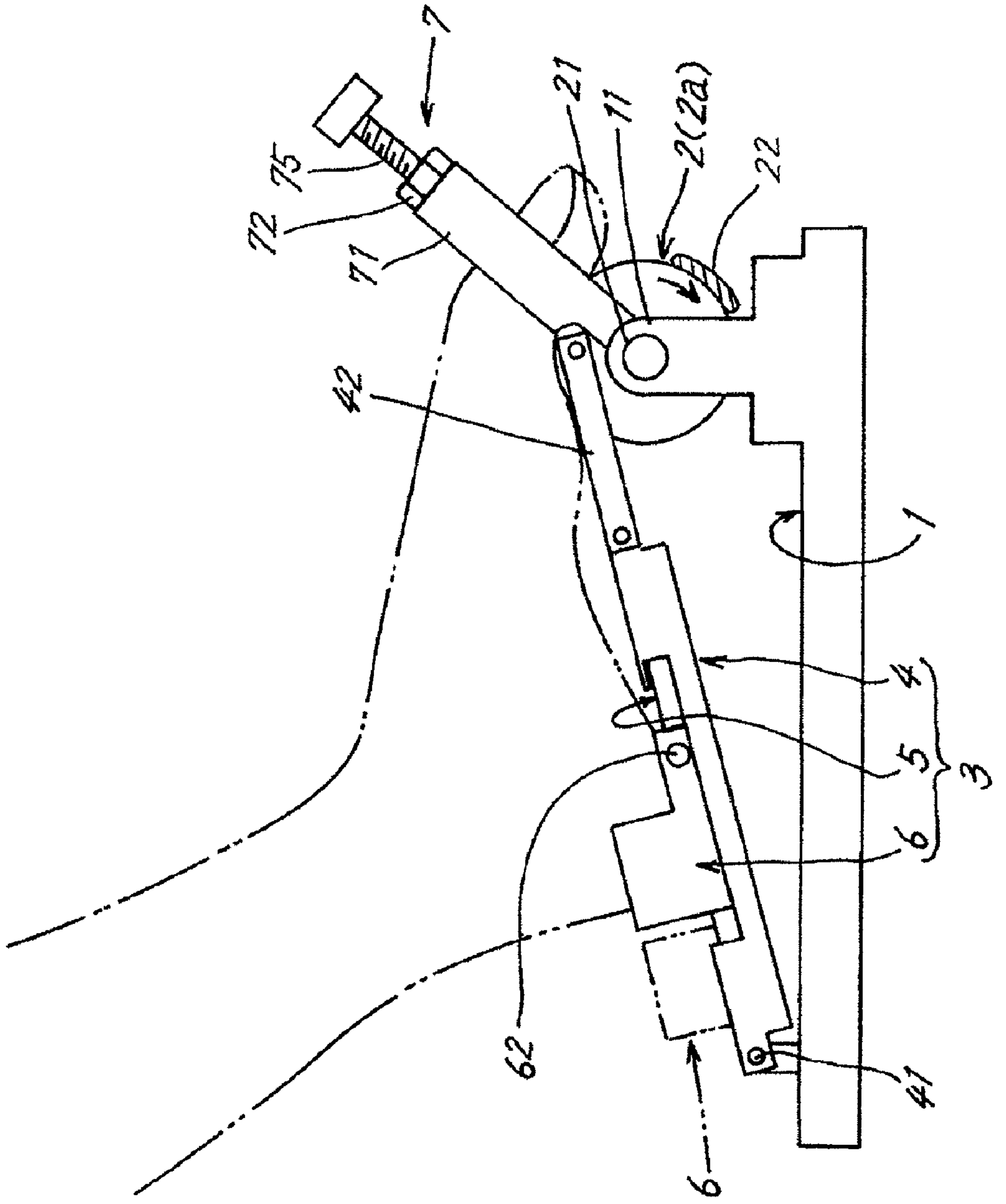
FIG. 5 is a side view of the toe massage device in which the rotating body is in a toe pulling position.

FIG. 5 shows a state where the rotating body (2) is in a toe pulling position. The toe fixation means (7) is inclined in a direction pulling the toes. The swinging member (4) and the links (42) are located in substantially the same straight line, and the free end of the swinging member (4) rises most.

Figure 6:
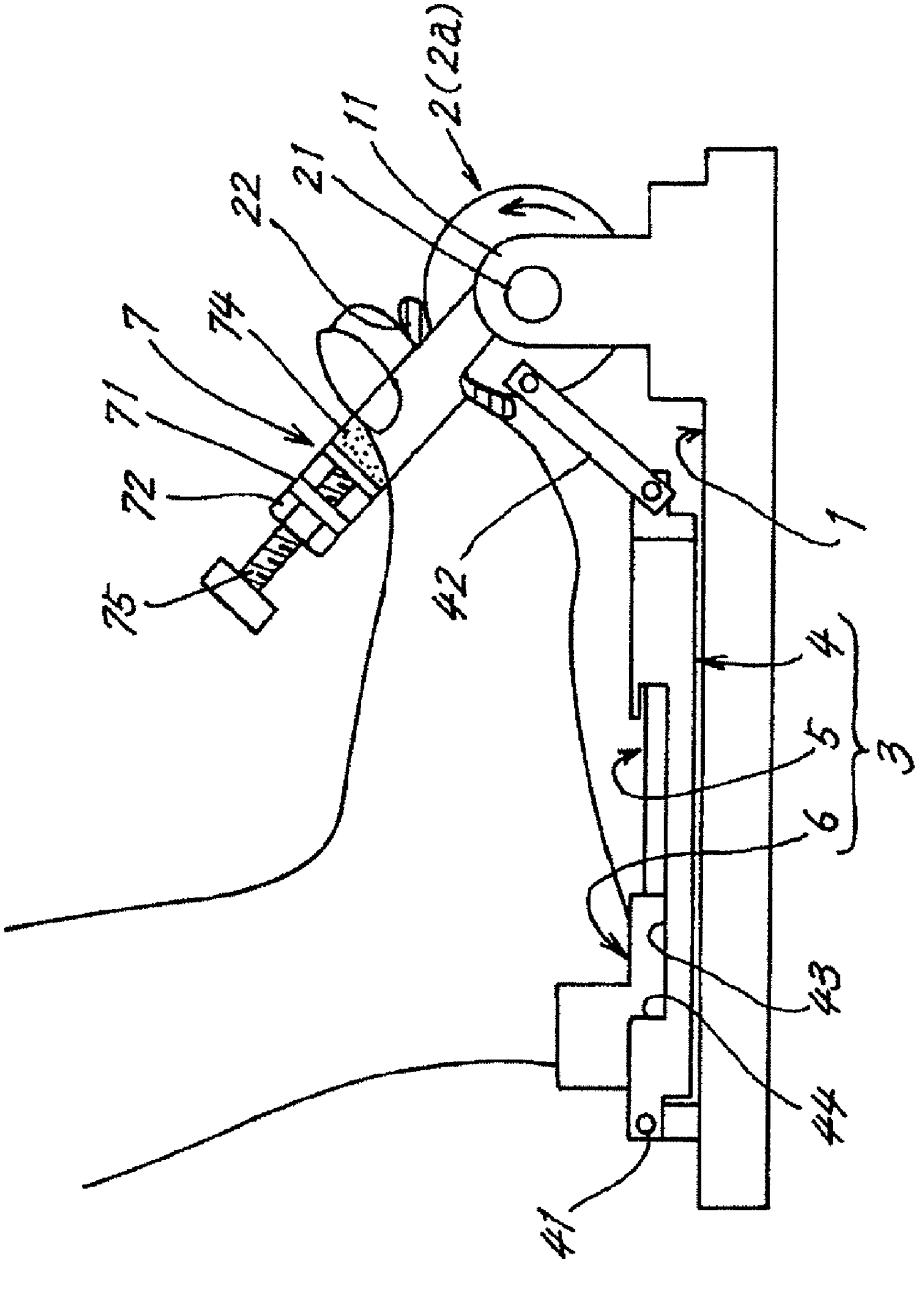
FIG. 6 is a side view of the toe massage device in which the rotating body is in a toe bending-back position.

FIG. 6 shows a state where the rotating body (2) is in a toe bending-back position. The toe fixation means (7) is inclined in a direction compressing the toes. The swinging member (4) is in a state substantially parallel to the base (1), and the free end of the swinging member (4) is in a lowest position.

According to commands from a controller of a remote-control type, the above-described rotation drive device (8) can make setting of the neutral position of the rotating body (2), setting of a clockwise rotation angle (rotation angle of rotation in the normal direction) from the neutral position, setting of a counterclockwise angle (rotation angle of rotation in the reverse direction) from the neutral position, setting of a reciprocating rotation period of the rotating body (2) and the like.

However, the controller may be eliminated to fix the angle of rotation in the normal and reverse directions of the rotating body (2) to a certain range. In this case, in view of the size of the above-described roller (2*a*), the rotation angle of the rotating body (2) is appropriately set to about 45° from the neutral position in the respective normal and reverse directions.

When the toe massage device is used, as shown in FIG. 4, a heel of one of the feet is rested on the sole rest member (6). Next, five toes are inserted between the pressing member (73) of the toe fixation means (7) and the rotating body (2) in the neutral position.

Since a length from the heel to each of the toes becomes shorter in order from the first toe (thumb) to the fifth toe (minimus), when the sole rest member (6) is fixed, it is difficult to simultaneously insert the five toes between the rotating body (2) and the pressing member (73). If the position of the sole rest member (6) is fixed so that the five toes can be simultaneously inserted between the rotating body (2) and the pressing member (73), this poses problems that this device cannot be used for the other foot, and that the device cannot correspond to a variation in size of foot.

In the embodiment, the sole rest member (6) is disposed on the rotating member (5) that can rotate on the swinging member (4). Thereby, when the heel of the foot can be rested on the sole rest member (6), and sole rest member (6) is moved so as to insert all the five toes between the rotating body (2) and the pressing member (73), the five toes can be easily inserted between the rotating body (2) and the pressing member (73). Additionally, since the sole rest member (6) can approach, and draw apart from, the rotating body (2), this device can be used for any size of foot.

Once the five toes are inserted between the rotating body (2) and the pressing member (73), the push bolt (75) is fastened to sandwich and hold the toes by the rotating body (2) and the pressing member (73).

Although thickness of the five toes differs, the elastic members (22) (74) are placed in the respective opposed portions of the rotating body (2) and the pressing member (73), so that the elastic deformation of the elastic members (22) (74) allows the respective toes to be sandwiched and held in just proportion. This can prevent the toes from being hurt due to excessive strong fastening force.

The rotating body (2) can be rotated in the normal and reverse directions by the rotation drive device (8).

As shown in FIG. 5, when the rotating body (2) rotates in the normal direction, the toes are pulled and bent downward, that is, to the sole side along a circular arc surface of the rotating body (2).

The entire sole is also pulled obliquely upward on the rotating body (2) side. At this time, the sole rest member (6) on which the heel is rested swings upward in conjunction with the rotation of the rotating body (2) so as to follow in the pull direction of the toes. Therefore, large load is not applied to the toes, which can prevent the toes from being hurt.

Additionally, since the sole rest member (6) can approach, and draw apart from, the rotating body (2), the sole rest member (6) slides in the pull direction, so that excessive load is not applied to the foot.

As shown in FIG. 6, the rotating body (2) rotates in the reverse direction, a force bending the toes back to the instep side is applied. A force pushing the sole in the direction apart from the rotating body (2) and a downward force act on the entire sole. At this time, the sole rest member (6) moves back in the pushed direction, and swings downward centering around the spindle (41), so that excessive load is not applied to the foot.

As described above, when the rotating body (2) rotates in the normal and reverse directions, respectively, the bending of the toes to the sole side and the bending-back to the instep side are performed alternately. Additionally, these motions involve the motions of the pull and compression of the toes. These combined motions cannot be attained in a conventional automatic massage device, which makes the subject feel as if he or she were massaged by a massager.

Moreover, the subject only needs to fix his or her toes on the rotating body (2), and since the rotating body (2) is automatically rotated in the normal and reverse directions to perform the above-describe massage by the rotation drive device (8), the subject can receive the massage in a comfortable position while sitting on a chair.

For example, when a vibratory device (not shown) such as a vibrating motor is linked to the rotating body (2) so that the rotating body (2) is rotated in the normal and reverse directions while being vibrated, a massage effect by vibration can be attained in addition to the above-describe effect. In this case, the supporting shaft (21) of the rotating body (2) needs to be supported by the brackets (11) of the base (1) so as to vibrate and rotate in the normal and reverse directions. The vibrating motor can also be mounted inside of the rotating body (2).

As described above, if the sole rest member (6) freely approaches, and draws apart from, the rotating body (2) by the forces acting on the sole, the effects of the pull and compression of the toes by the normal and reverse rotations of the rotating body (2) will be reduced. For the subject who feels the effect of the massage weak, by providing means for fixing the sole rest member (6) in an optimal position of the guide line (52), the pull force, compression force, bending force to the sole side, and bending-back force to the instep side of intensities desired by the subject can be attained.

Figure 2:
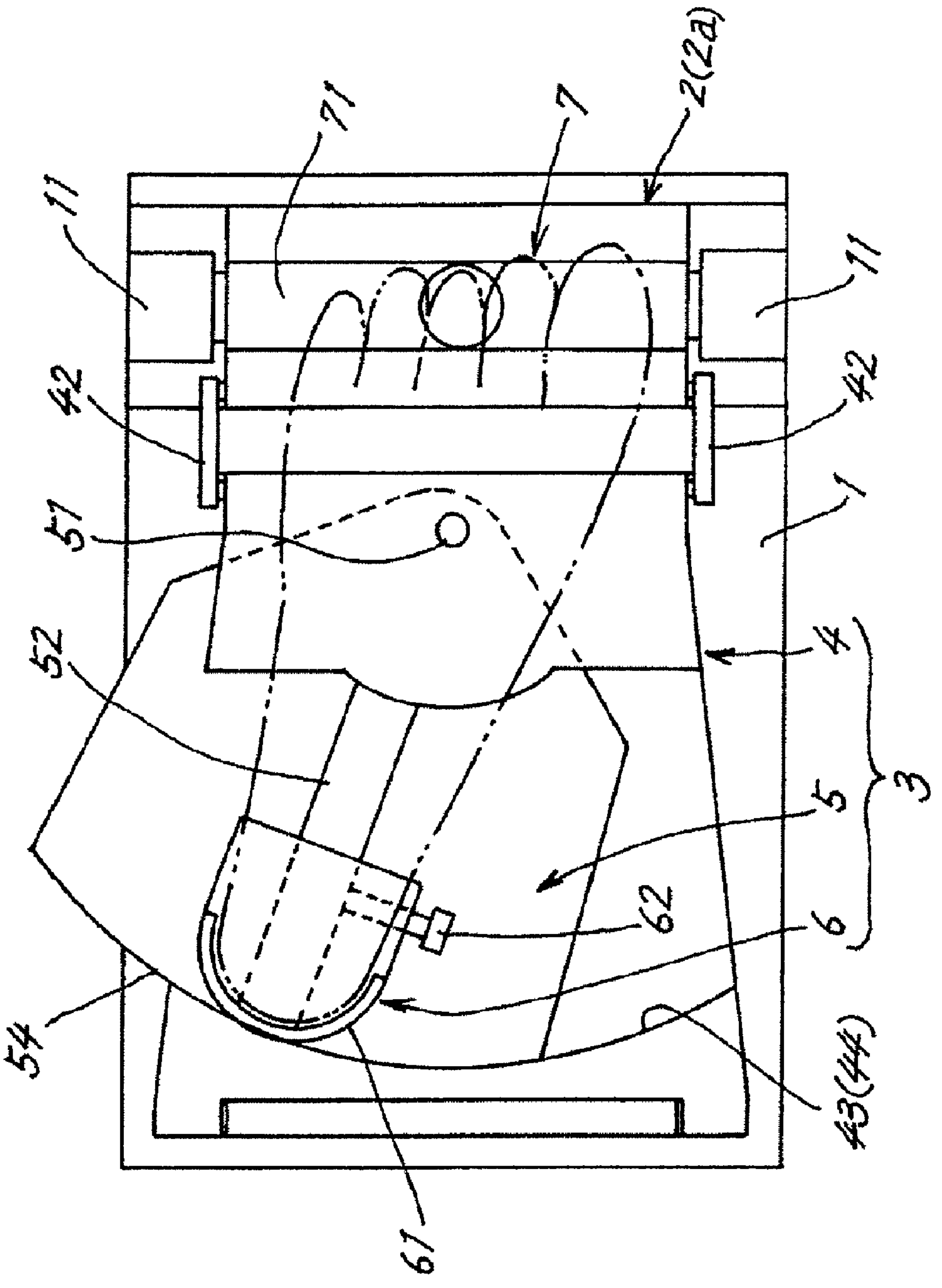
FIG. 2 is a plan view of a state where an angle of a sole rest member of the same is changed.

As the fixation means of the sole rest member (6), for example, as shown in FIGS. 2 and 5, there can be cited means in which a clamping bolt (62) capable of pressing a side surface of the guide line (52) is screwed into the sole rest member (6). The clamping bolt (62) is fastened to thereby fix the sole rest member (6) in an optimal position on the guide line (52).

While the rotating body (2) is a roller in the embodiment, it is not limited to this, but the rotating body (2) can have any shape, if it can play a role of a supporting table for rotating the toe fixation means (7) in the normal and reverse directions. In a constitution in which the toe fixation means (7) is rotated directly by the rotation drive device (8), the toe fixation means (7) also serves as the rotating body (2).

The invention claimed is:

1. A toe massage device comprising: a roller rotatably supported about a lateral supporting shaft on a base; a rotation drive device that rotates said roller in normal and reverse directions; toe fixation means provided on the roller for fixing toes of a subject on the roller; and a footrest for resting a foot of the subject, whereby the toe massage device repeatingly massages by pull bending and press bending-back with respect to the toes of the subject, wherein the footrest comprises:

a plate-like swinging member having a free end side linked to the roller; an opposite end side that is opposite to the free end side; and a horizontal spindle on the opposite end side, wherein the free end side swings vertically pivoting around the horizontal spindle in conjunction with the rotation of the roller;

a rotating member rotating around a pivot, the pivot being located in a center of a width on the free end side of the swinging member and oriented in a direction perpendicular to the supporting shaft of the roller; and a heel rest member disposed on the rotating member and on which a heel of the subject is rested.

2. The toe massage device according to claim 1, wherein the heel rest member is disposed on the rotating member so as to move closer to and away from the roller.

3. The toe massage device according to claim 1, wherein the toe fixation means is constructed by screwing a push bolt toward the supporting shaft of the roller on an attachment frame provided above the roller, and attaching a pressing member to a tip end of said push bolt, and the roller and the pressing member sandwich and hold the toes of the subject.

4. The toe massage device according to claim 1, wherein elastic members are placed in opposed portions of the toe fixation means, and the roller.

5. The toe massage device according to claim 1, wherein the roller is linked to a vibratory device to rotate in the normal and reverse directions with vibration.

6. The toe massage device according to claim 1, wherein the swinging member has a guide depressed portion and the rotating member is fitted into the guide depressed portion so as to rotate around the pivot with a convex arc wall surface of the rotating member in contact with a concave arc wall surface of the guide depressed portion.

* * * * *